(12) United States Patent
Fraga Trillo et al.

(10) Patent No.: US 6,875,615 B2
(45) Date of Patent: Apr. 5, 2005

(54) SENSORS FOR THE DETERMINATION OF ORGANOMETALLIC COMPOUNDS

(75) Inventors: Luisa Maria Fraga Trillo, Madrid (ES); Valentin Ruiz Santa Quiteria, Madrid (ES); Guillermo Orellana Moraleda, Madrid (ES); Ana Maria Castro Franco, Madrid (ES)

(73) Assignee: Dynasol Elastomeros, S.A., Madrid (ES)

( * ) Notice: Subject to any disclaimer, the term of this patent is extended or adjusted under 35 U.S.C. 154(b) by 0 days.

(21) Appl. No.: 10/125,006

(22) Filed: Apr. 17, 2002

(65) Prior Publication Data

US 2002/0151081 A1 Oct. 17, 2002

(30) Foreign Application Priority Data

Apr. 17, 2001 (EP) ............................................ 01500101

(51) Int. Cl.$^7$ ............................................... G01N 33/20
(52) U.S. Cl. ...................... 436/76; 422/56; 422/82.05; 436/73; 436/77; 436/79; 436/80; 436/81; 436/82; 436/83; 436/84; 436/166; 436/169; 436/172
(58) Field of Search ............... 422/56–58, 82.05–82.09; 436/73, 76–77, 79–84, 166, 169, 172

(56) References Cited

U.S. PATENT DOCUMENTS

| | | | | |
|---|---|---|---|---|
| 3,290,116 A | * | 12/1966 | Carroll | ......................... 526/59 |
| 4,853,090 A | * | 8/1989 | Daniel et al. | ............. 205/781.5 |
| 5,212,099 A | * | 5/1993 | Marcus | ........................ 436/172 |
| 5,350,518 A | * | 9/1994 | Hiti et al. | .................... 210/638 |
| 5,350,694 A | * | 9/1994 | Zimmerle | ....................... 436/2 |
| 5,464,587 A | * | 11/1995 | Lippitsch et al. | ........ 422/82.07 |
| 5,650,331 A | * | 7/1997 | Jorgensen et al. | ........... 436/163 |

FOREIGN PATENT DOCUMENTS

CN 1216368 * 5/1999

OTHER PUBLICATIONS

Eppley, R. L. et al.,Journal of Organometallic Chemistry 1967, 8, 176–8.*
Narayanaswamy, R. et al, Analyst 1986, 111, 1085–8.*
Sugihara, H. et al, Chemistry Letters 1987, 2391–2.*
Saito, T. Analytica Chimica Acta 1992, 268, 351–5.*
Sugihara, H. et al, Analytical Sciences 1993, 9, 593–7.*
Maksimova, I. M. et al, Juornal of Analytical Chemistry 1994, 49, 628–631.*
Okada, T. et al, Analyst 1995, 120, 2381–6.*
Sugihara, H. et al, Coordination Chemistry Reviews 1996, 148, 285–299.*

(Continued)

*Primary Examiner*—Arlen Soderquist
(74) *Attorney, Agent, or Firm*—Ladas & Parry LLP (57) ABSTRACT

The present invention relates to sensors for the determination of organometallic compounds comprising the following elements:
a) an inorganic, organic or polymeric support, insoluble in the sample to analyze
b) an indicator which reversibly reacts with the organometallic compound and whose reaction product gives a characteristic absorption, reflection or emission band in the range 150–15000 nm and which is physically trapped, adsorbed, absorbed, dissolved or chemically linked in an electrostatic or covalent way to the support
c) an optical sensor which measures the absorption, reflection or emission of the functionalized support at the characteristic wavelength and transforms it in the concentration of the organometallic present in the solution.

Also described is the method for the determination of the concentration of organometallic compounds by the on line use of a sensor as above defined.

10 Claims, 5 Drawing Sheets

OTHER PUBLICATIONS

Mohr, G. J. et al, Analytica Chimica Acta 1998, 360, 119–128.*

Ervin, A. M. et al, Sensors and Actuators, B 1998, 53, 104–110.*

Carter, M. T. et al, SPIE 1999, 3540, 123–133.*

Van Vliet, G. L. J. et al, Angewandte Chemie, International Edition 2000, 39, 1643–1645.*

Hiratani, K. et al, Busshitsu Kogaku Kogyo Gijutsu Kenkyusho Hokoku 1994, 2, 499–576.*

* cited by examiner

SENSORS FOR THE DETERMINATION OF ORGANOMETALLIC COMPOUNDS

FIELD OF THE INVENTION

The invention refers to sensors useful for organometallic compounds determination and to the on line spectroscopic monitorization of such reactive species, particularly in anionic polymerization initiated by organolithium compounds or any other reaction that involves an organometallic compound being critical the stoichiometry of the same.

BACKGROUND OF THE INVENTION

As described in the prior art, there are several methods for the determination of organolithium compounds.

Kofron and Baclawski [Kofron, W. G.; Baclawski, L. M.; J. Org. Chem. 1976, 41, 1879] describe the use of diphenyl acetic acid as colorimetric indicator.

As alternatives to diphenyl acetic acid, similar indicators have been proposed. 4-biphenylyl methanol, 4-biphenylyl acetic acid [Juaristi, E.; Martínez-Richa, A.; García Rivera, A.; Cruz-Sánchez, J. S.; J.Org. Chem. 1983, 48, 2603], and 1-pyreneacetic acid [Kiljumen, H.; Hase, T. A.; J.Org.Chem. 1991, 56, 6950] have been used as indicator molecules for the titration of organolithium compounds providing a clearer visual detection of the equivalence point due to a more extended delocalization of the charge in the coloured final dianions.

In the same way, Winkle et al. [Winkle, M. R.; Lansinger, J. M.; Donald, R. C.; J. Chem. Soc. Chem. Commun. 1980, 87] have used 2,5-dimethoxybenzyl alcohol as indicator for the titration of organolithium reagents, resulting in the formation of visually detectable coloured dianionic species.

More recently, new titration methods for the determination of alkyl- and aryllithium compounds based on the double deprotonation of different colorimetric indicators have been reported. This is the case of the procedure described by Suffert [Suffert, J.; J.Org.Chem. 1989, 54, 509] proposing N-pivaloyl-o-toluidine and/or N-pivaloyl-o-benzyl aniline as indicator dyes.

Another group of indicators that undergo a double deprotonation upon reacting with lithium organometallic compounds include benzenesulphonyl- and tosylhydrazone derivatives [Miranda, R.; Hernández, A.; Angeles, E.; Cabrera, A.; Salmón, M.; Joseph-Nathan, P.; Analyst, 1990, 115, 1483].

Another possibility of determining organolithium compounds by colorimetric titration is based on the single deprotonation of triphenylmethane [Eppley, R. L.; Dixon, J. A.; J. Organomet. Chem 1967, 8, 176], N-benzylidenbenzylamine [Duhamel, L.; Plaqevant, J. C.; J.Org.Chem. 1981, 44, 24304] or N-phenyl-1-naphthylamine [Bergbreiter, D. E.; Pendergrass, E.; J.Org.Chem. 1981, 46, 219] to yield, after reaction with the organolithium compound, the corresponding coloured anions that can be back-titrated with sec-butyl alcohol or benzoic acid solution.

Moreover, the fact that alkyl organolithium and organomagnesium compounds form coloured complexes with different Lewis bases, all of them having extended π or aromatic structure, provides us one of the more used optical methods for the titration of such organometallic compounds. The charge-transfer complexes obtained in this way display an intense absorption in the visible region of the electromagnetic spectrum. The most common polycyclic aromatic bases used to that end are 1,10-phenanthroline and 2,2-biquinoline [Watson, S. C.; Eastham, J. F.; J.Organomet.Chem. 1967, 9, 165].

On the other hand, industrial anionic polymerization initiated by organolithium compounds is one of the more versatile methods for synthesizing macromolecules due to the possibility of designing very different chemical structures for many applications, but an strict control of the process is required. Living anionic polymerization of 1,3-conjugated diene and/or monoalkenyl aromatic hydrocarbon, allows us to synthesize macromolecular compounds with a high control of their composition and structural parameters such as molecular weight distribution, microstructure, stereochemistry, branching and chain functionalization. The molecular weight of the polymer is one of the most important variables that affect the macromolecular properties. In a living anionic polymerization, the molecular weight is determined by the reaction stoichiometry and the conversion rate. This solution polymerization process is extremely sensitive to impurities in the reaction medium that can modify the effective initiator concentration or the number of growing chains. That is the reason why one of the main parameters to be controlled in such processes is the so called reaction threshold, namely, the amount of initiator consumed by impurities or "poisons" able to react with it before the initiation step is effective.

Therefore, according to the background, a method based on sensors useful for titration of organolithium compounds by spectroscopic monitorization of reactive species has not been described up to date, with particular application to anionic polymerization processes initiated by organolithium compounds or any other process that involves an organometallic compound being critical the stoichiometry of this compound.

DETAILED DESCRIPTION OF THE INVENTION

A fiber-optic sensor is a device able to measure a physical parameter or to determine the concentration and/or activity of a chemical species "in situ", continuously and in real time, through an optical fiber, using the variation of the optical properties of a reagent phase. This sensing phase is placed in the sensitive terminal (that could be the optical fiber with an optical indicator), whose optical properties vary on contacting a chemical stimulus.

These optical sensors allow us to titrate organometallic compounds and to monitor the neutralization point of all the impurities that destroy the initiator used in the anionic polymerization of 1,3-conjugated dienes and/or monoalkenyl aromatic hydrocarbons or any other process that involves an organometallic compound being critical to the stoichiometry of the same. The procedure implies a continuous, "in situ" and real-time measurement of the reaction threshold in contrast with the conventional method based on taking out and analyzing the sample that has some inherent limitations (slowness, discontinuity, manipulation required, . . . )

It has been found that different combinations of indicator and support can be used to design sensors for the determination of organometallic compounds.

The sensitive terminal is the most important element in the construction of a so-called chemical sensor because it contains the reactive phase or sensitive layer. This reactive phase can be located either at the distal end of the optical fiber or inserted into the cladding of the fiber core or in the evanescent wave region, replacing part of the fiber cladding. An improvement in the sensor sensitivity and/or selectivity can be achieved by confining the reactive phase using a membrane to separate it from the analyte phase or a permeable polymer as the indicator support or by covalent binding of the indicator dye to long chain polymers that improve the accessibility of the analyte.

Therefore, an object of the present invention is the provision of an optical sensor useful for the qualitative and/or quantitative determination of organometallic compounds, specially organometallic compounds wherein the metal is a metal of groups 1, 2 and 13 of the Periodic Table of the Elements, preferably for the determination of organolithium compounds.

Another object of the present invention is the provision of an optical sensor useful for the determination of the reaction threshold in the anionic polymerization of a 1,3-conjugated diene and/or monoalkenyl aromatic hydrocarbon copolymer, namely the amount of initiator consumed by impurities or "poisons" able to react with it before the initiation step is effective or any other reaction that involves an organometallic compound being critical the stoichiometry of the same.

The sensor for the qualitative and/or quantitative determination of organometallic compounds according to the present invention comprises the following elements:

a) an inorganic, organic or polymeric support insoluble in the sample to analyze;

b) an indicator which reversibly reacts with the organometallic compound and whose reaction product gives a characteristic absorption, reflectance or emission band in the range 150–15000 nm, preferably 200–800 nm and which is physically entrapped, adsorbed, absorbed, dissolved or chemically bound in an electrostatic or covalent way to the support; and c) an optical sensor which measures the absorption, reflectance or emission of the functionalized support at the characteristic wavelength and transforms it in the concentration of the organometallic present in the solution.

The optical indicator dye, whose absorbance, reflectance or emission will change in the presence of organometallic compounds, belongs preferably to heterocyclic aromatic compounds (for example 1,10-phenanthroline, 5-amino-1, 10-phenanthroline, 5-nitro-1,10-phenanthroline, 4,7-dimethyl-1,10-phenanthroline, 4,7-diphenyl-1,10-phenanthroline, 5-hydroxy-1,10-phenanthroline, sodium 1,10-phenanthroline-4,7-di(phenylsulphonate), 5-perfluorooctanamide-1,10-phenanthroline, 4-vinyl-7-methyl-1,10-phenanthroline), N-(2-methyl)-2,2-dimethylpropanamide, N-[2-(4-hydroxybenzyl) phenyl]-2, 2-dimethylpropanamide, N-(2-benzylphenyl) perfluorooctanamide, N-[4-(2-(2,2-dimethylpropanoylamine)benzyl)phenyl]-perfluorooctanamide) or triarylmethane derivatives (for example 4,4'-(difluorophenyl) phenylmethane and triphenylmethane).

The indicator supports can be of very different chemical composition but can be preferably classified by its inorganic (for example, silicagel, powdered porous glass, porous glass layer, poly(dimethylsiloxanes), silicic xerogels) or organic (for example, poly(tetrafluoroethylene), poly(vinyl chloride), Nafion® membranes, styrene-divinylbenzene copolymers) nature.

The preferred immobilization procedures are adsorption for poly(tetrafluoroethylene) [Blair, T. L.; Cynkowski, T.; Bachas, L. G.; Anal.Chem. 1993, 65, 945] and Nafion® [García-Fresnadillo, D.; Marazuela, M. D.; Moreno-Bondi, M. C.; Orellana, G.; Langmuir, 1999, 15, 6451; Garcia-Fresnadillo, D.; Tesis Doctoral, Universidad Complutense de Madrid, Madrid, 1996] supports, embedment for poly(vinyl chloride) membranes [Bakker, E.; Bühlmann, P.; Pretsch, E.; Chem.Rev. 1997, 97, 3083; Seiler, K.; Simon, W.; Anal.Chim. Acta, 1992, 266, 73; Seiler, K.; in "Ion-Selective Optode Membranes"; Fluka Chemie A. G., Buchs, Suiza, 1993 (Fluka N° 58166); Morf, W. E.; Seiler, K.; Lehman, B.; Behringer, Ch.; Hartman, K.; Simon, W.; Pure Appl. Chem. 1989, 61, 1613; Eugster, K.; Rosatzin, T.; Rusterholz, B.; Aebersold, B.; Pedrazza, V.; Rüegg, D.; Schmid, A.; Spichiger, U.; Simon, W.; Anal. Chim. Acta. 1994, 289,1; Okada, T.; Sugihara, H.; Hiratani, K.; Analyst, 1995, 120, 2381] and silicic sol-gel materials [Lev, O.; Tsionsky, M.; Rabinovich, L.; Glezer, V.; Sampath, S.; Pankratov, I.; Gun, J.; Anal. Chem. 1995, 67, 22A; Avnir, D.; Levy, D.; Reisfeld, R.; J.Phys.Chem. 1984, 88, 5956; Aylott, J. W.; Richardson, D. J.; Russell, D. A.; Chem.Mater. 1997, 2, 2261; Habilo Jiwan, J.-L.; Soumillion, J.-Ph.; J.Non-Cryst.Solids 1997, 220, 316; Wallington, S. A.; Pilon, C.; Wright, J. D.; J.Sol-Gel Sci.Tech. 1997, 8, 1127; Isoefzon-Kuyasuskava, B.; Gigozin, I.; Ottolenghi, M.; Avnir, D.; Lev, O.; J.Non-Crys.Solids 1992, 147, 808; Klein, L. C. in Sol-Gel Optics: Processing and Applications, Kluwer Academic Publisher, Norwell, Mass., 1994] and covalent binding for silicagel [Locke, D. C.; J.Chromatographic Sci. 1973, 11, 120; Brust, O. E.; Sebestian, I.; Halasz, I.; J.Chromatography 1973, 83, 15; Locke, D. C.; Schmermu, J. T.; Banner, B.; Anal. Chem. 1971, 60, 329; Yam, C. M.; Kakkar, A. K.; J.Chem.Soc., Chem.Commun. 1995, 907], porous glass [Locke, D. C.; J.Chromatographic Sci. 1973, 11, 120; Brust, O. E.; Sebestian, I.; Halasz, I.; J.Chromatography 1973, 83, 15; Locke, D. C.; Schmermu, J. T.; Banner, B.; Anal. Chem. 1971, 60, 329; Xavier, M. P.; Garcia-Fresnadillo, D.; Moreno-Bondi, M. C.; Orellana, G.; Anal.Chem. 1998, 70, 5184; Basile, L. A.; Barton, J. K.; J. Am. Chem. Soc. 1987, 109, 7458; Howells, R. D.; McCown, D. J.; Chem. Rev. 1977, 77, 69; Efferberger, K.; Huthnacher, K.; Angew. Chem. Int. Ed. Engl. 1974, 13, 409] and styrene copolymers [Arnold, M. A.; Anal.Chem. 1992, 64, 1015A; Frechet, J. M. J.; Farrall, M. J; in The Chemistry and Properties of Crosslinked Polymers, (S. S. Labana, ed.), Academic Press, New York, 1977; p.59; Neckers, D. C.; Kooistra, D. A.; Green, G. W.; J. Am. Chem. Soc. 1972, 94, 9284].

The indicator chemistry of the sensors disclosed in this invention can be classified, according to the type of interaction between the analyte and the reactive phase, as formation of a complex (for example with the couples 5-hydroxy-1,10-phenanthroline/silicagel, sodium 1,10-phenanthroline-4,7-di(phenaylsulphonate)/porous glass, 1,10-phenanthroline/silicic sol-gel materials, 1,10-phenanthroline/Nafion® and vinyl-phenanthroline/styrene-divinylbenzene) or an acid-base reaction (for example N-[2-(4-hydroxybenzyl)phenyl]-2,2-dimethylpropanamide/silicagel, N-(2-benzylphenyl)perfluorooctanamide/polytetrafluoroethylene, 5-perfluorooctanamide-1,10-phenanthroline/Nafion® and triphenylmethane/Amberlite®).

The sensor according to the invention is stable within a range of temperature that is characteristic of the support/indicator system. If the sensor is not stable at the reaction temperature, it is possible to locate the sensor in a thermostated loop, maintained in constant circulation with the reactor or medium where the polymerization or organic reaction take place.

The sample to be analysed comprises a solution of the organometallic to be determined in a suitable solvent.

The sensor according to the present invention may be used for the qualitative and/or quantitative determination of organometallic compounds, specially organometallic compounds wherein the metal is a metal of groups 1, 2 or 13 of the Periodic Table of the Elements, in, for example, industrial and laboratory chemical synthesis. In a particular embodiment, the sensor according to the present invention is useful for the determination of the neutralization point of all impurities that destroy the organolithium initiator in anionic polymerization processes or any other chemical reaction that involves an organolithium compound in an organic medium.

Another object of the present invention is the method, based on the use of an optical sensor, useful for detemining organolithium compounds and particularly for determining the reaction threshold in the anionic polymerization of a 1,3-conjugated diene and/or monoalkenyl aromatic hydrocarbon copolymer initiated by organolithium compounds or any other reaction that involves an organometallic compound being critical the stoichiometry of the same.

The method comprises contacting the sensor according to the present invention with the sample to be analysed under conditions wherein the indicator reversibly reacts with the organometallic compound to render a reaction product having a characteristic absorption, reflectance or emission band in the range between 150 nm and 15000 nm, and measuring the absorption, reflectance or emission of the functionalized support at the characteristic wavelength and transforming it in the concentration of the organometallic compound present in the solution.

In a particular embodiment, the method for the determination of the concentration of organometallic compounds is characterized by the on-line use of a sensor according to the present invention, the sensor being located in a thermostated loop, mantained in constant circulation with the reactor and the measurement being made directly in the reaction medium.

The method may be applied for the determination of the neutralization point of all the existing impurities that can destroy the organometallic initiator in the anionic polymerization of a 1,3-conjugated diene and/or monoalkenyl aromatic hydrocarbon copolymer initiated by organolithium compounds. The method may also be applied for the determination of organometallic compounds in industrial and laboratory chemical synthesis.

EXAMPLES

Experimental Method

All the tests which are described in the present invention were carried out in a polymerization reactor with a capacity of 1 or 20 liters, provided with conditioning systems for nitrogen, venting and thermostating. Although it is possible to work in a continuous or semicontinuous mode, in this case a batch operation was used, i.e. a discontinuous mode. Raw materials were purified using the methods described in the state of the art (for example distillation, drying, etc.).

Example 1

This example corresponds to the determination of n-butyllithium using a fiber-optic sensor according to the object of the invention.

The fiber-optic sensor is composed by the following elements:

Indicator: N-[2-(4-hydroxybenzyl)phenyl]-2,2-dimethylpropanamide (HBPD). This indicator dye is prepared: firstly according to the general procedure of aromatic amines o-functionalization described by Fuhrer and Gschwend [Fuhrer, W.; Gschwend, H. W.; J.Org.Chem. 1979, 44, 1133; Gschwend, H. W.; Rodriguez, H. R.; Org. React. 1979, Vol.26], secondly, the nitrocompound is reduced with hydrazine monohydrate using the method described by Nasielski-Hinkens et al. [Nasielski-Hinkens, R.; Benedeck-Vamos, M.; Maetens, D.; J.Heterocycl. Chem. 1980, 17, 873]; finally, the diazonium salt is prepared using sodium nitrite and sulphuric acid and then is neutralized with sulphuric acid in water, obtaining the phenol.

Support: Silica gel

Immobilization procedure: Covalent. The method followed to functionalize silicagel supports is based on the matrix surface chemical modification with amine-Si or amine-Sn groups [Yam, C. M.; Kakkar, A. K.; J. Chem. Soc., Chem. Commun. 1995, 907] [Fessenden, R.; Fessenden, J. S.; Chem. Rev. 1961, 61, 361] [Jones, K.; Lappert, M. F.; in "Organotin Compounds", Vol.2, Ed. A. K. Sawyer, Marcell Dekker, Inc., New York, 1977; p.150]. These groups will let us bind the different cromophores to the support with an stable, for example in anionic polymerization conditions, ether bond.

Measurement principle: Reflectance

Once the sensitive terminal is prepared, by placing it at the distal end of a fiber-optic, it was introduced into the sample solution or reaction medium. The method consists in the addition of different aliquots of n-butyllithium (i.e. 1.6 M in cyclohexane solution) into a closed and nitrogen inertized reaction vessel with the sample to titrate, up to the detection of chromophore species, monitored by an spectrophotometer connected to the fiber-optic.

Figure 1:
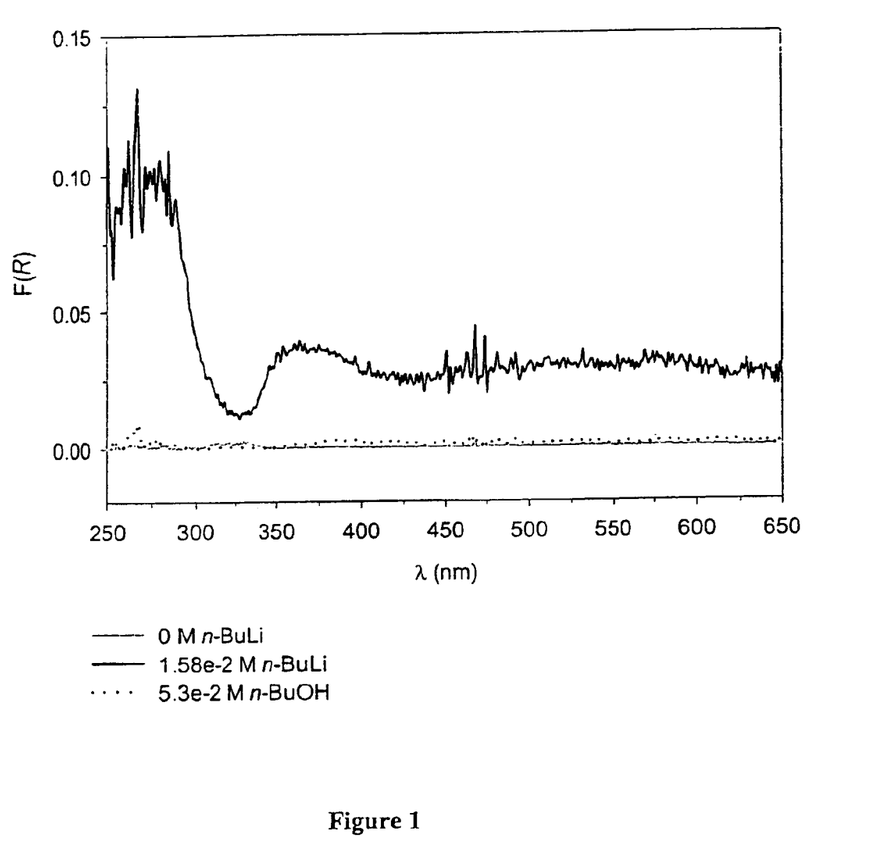
FIG. 1 shows the variation of the Kubelka-Munk reflectance function, F(R), of the HBPD immobilized on silica gel, as a function of the final n-butyllithium concentration added.

FIG. 1 shows the variation of the Kubelka-Munk reflectance function, F(R), of the HBPD immobilized on silica gel, as a function of the final n-butyllithium concentration added.

As it is shown in FIG. 1, there is not reflectance observed if no n-butyllithium is added (–0 M n-BuLi, reference baseline). Subsequently, the presence of species existing in the reaction medium that can kill the n-butillithium does not allow the appearance of any reflectance in the spectra up to a concentration of $1.58 \times 10^{-2}$ M of added n-butyllithium (–1.58e–2 M n-BuLi) with the appearance of a maximum F(R) at 370 nm. This maximum value is associated to full reaction of the immobilized indicator (HBPD) with the active n-butyllithium, that remains after the stoichiometric neutralization of all the poisons.

This could be the control starting point from which all the n-butyllithium added would act as active initiator of anionic polymerization or other reaction that involves this kind of compounds.

FIG. 1 also shows that after addition of a known amount of n-butanol (... 5,3e−2 M n-BuOH, in FIG. 1) the complex is destroyed, reflectance of initial base line is recovered and the sensitive terminal can be used again.

According to the procedure described above, the determination of the concentration of an unknown solution of n-butyl-lithium can be performed by introducing a known amount ("A" mol) of an alcohol (e.g. n-butyl alcohol) as a proton donor into the inertized solvent where the optical sensor is placed. In this moment, the unknown n-butyl-lithium solution is added up to the point where the established criterion value of reflectance at 370 nm is achieved. The amount of n-butyllithium added ("C" milliliters of n-butyllithium solution) is equivalent to the known amount of n-butyl alcohol in mol. Therefore, the concentration of n-butyllithium in mol/l is calculated as:

Concentration of the n-butyllitium solution (mol/l)=$(A\times 64000)/C$

Example 2

This example corresponds to the determination of n-butyllithium using a fiber-optic sensor according to the object of the invention.

The fiber-optic sensor is composed by the following elements:

Indicator: Triphenylmethane (TPM)

Support: Highly crosslinked styrene-divinyl benzene copolymer (Amberlite® XAD-2).

Immobilization procedure: Covalent. The functionalization of styrene divinylbenzene copolymers is based on Friedel-Crafts alkylation of the polymer with diphenylmethyl chloride through the $AlCl_3$ complex in nitrobenzene [Neckers, D. C.; Kooistra, D. A.; Green, G. W.; J. Am. Chem. Soc. 1972, 94, 9284; Obrecht, D.; Villalgordo, J. M.; "Solid-Supported Combinatorial and Parallel Synthesis of Small Molecular Weight Compounds Libraries" in "Tetrahedron Organic Chemistry Series", Vol. 17, Pergamon Press, Oxford, 1998; Cap.1, pp. 28–45; Cohen, B. J.; Kraus, M. A; Patchornik, A.; J. Am.Chem.Soc. 1981, 103, 7620; Cohen, B. J.; Kraus, M. A.; Patchornik, A.; J. Am.Chem. Soc. 1977, 99, 4165]

Measurement principle: Reflectance

Once the sensitive terminal is prepared, by placing it at the distal end of a fiber-optic, it was introduced into the sample solution or reaction medium. The method consists in the addition of different aliquots of n-butyllithium (e.g. 1.6 M in cyclohexane solution) into a closed and nitrogen inertized reaction vessel with the sample to titrate, up to the detection of chromophore species, monitored by an spectrophotometer connected to the fiber optic.

Figure 2:
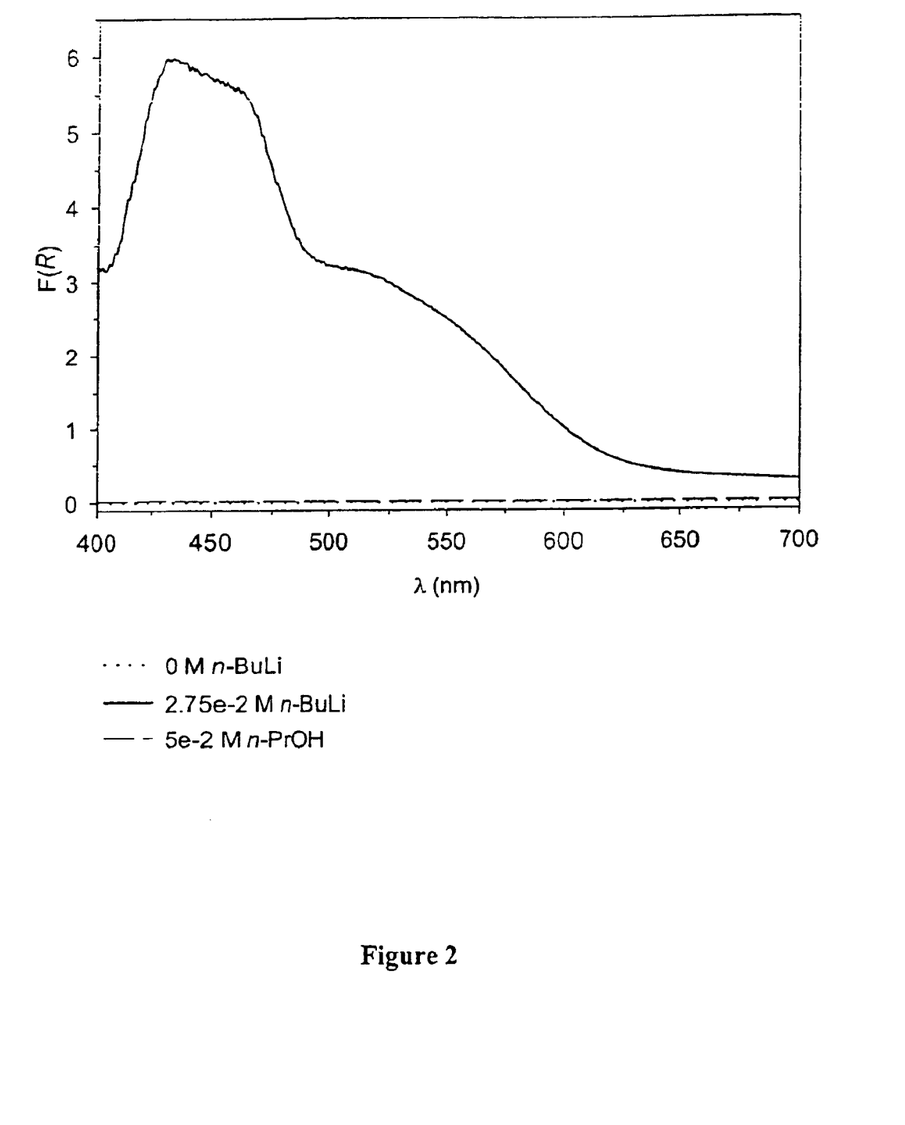
FIG. 2 shows the response of triphenylinethane covalently bound to Amberlite® XAD-2, at 25° after addition of n-butyllithium following the procedure of aliquots addition.

FIG. 2 shows the response of triphenylmethane covalently bound to Amberlite® XAD-2, at 25° C. after addition of n-butyllithium following the procedure of aliquots addition.

As it is shown in FIG. 2, there is not reflectance observed if no n-butyllithium is added (−0 M n-BuLi, reference baseline). Subsequently, the presence of species existing in the reaction medium that can kill the n-butillithium does not allow the appearance of any reflectance in the spectra up to a concentration of $2.75\times10^{-2}$ M of added n-butyllithium (−2.75e−2 M n-BuLi), showing a characteristic spectra of the chromophore formed by reaction of active n-butyllithium and the sensitive terminal, associated with triphenyl methane deprotonation. The reflectance value observed at 450 nm is taken as the control criteria, that represents the complete reaction of indicator and active n-butyllithium, being constant once the full neutralization of impurities or "poisons" is effective.

This could be the control starting point from which all the n-butyllithium added would act as active initiator of anionic polymerization or other reaction that involves this kind of compounds.

FIG. 2 also shows that after addition of a known amount of n-propanol ( ... 5,3e−2 M n-PrOH, in FIG. 2) the complex is destroyed, reflectance of initial base line is recovered and the sensitive terminal can be used again.

According to the procedure described above, the determination of the concentration of an unknown solution of n-butyl-lithium can be performed by introducing a known amount ("A" mol) of an alcohol (e.g. n-propyl alcohol) as a proton donor into the inertized solvent where the optical sensor is placed. In this moment, the unknown n-butyllithium solution is added up to the point where the established criterion value of reflectance at 450 nm is achieved. The amount of n-butyllithium added ("C" milliliters of n-butyllithium solution) is equivalent to the known amount of n-propyl alcohol in mol. Therefore, the concentration of n-butyllithium in mol/l is calculated as:

Concentration of the n-butyllitium solution (mol/l)=$(A\times 64000)/C$

Example 3

This example corresponds to homopolymerization of styrene with the previous reaction threshold determination using a fiber-optic sensor according to the object of the invention before the monomer and initiator addition to the reactor.

The fiber-optic sensor consists of the following elements:

Indicator: Sodium 1,10-phenanthroline-4,7-di (phenaylsulphonate) (S2D)

Support: Commercially available porous glass (PG) with different pore size containing γ-aminopropyl groups on its surface.

Immobilization procedure: Covalent [Xavier, M. P.; Garcíа-Fresnadillo, D.; Moreno-Bondi, M. C.; Orellana, G.; Anal. Chem. 1998, 70, 5184; Basile, L. A.; Barton, J. K.; J. Am.Chem. Soc. 1987, 109, 7458; Howells, R. D.; McCown, D. J.; Chem. Rev. 1977, 77, 69; Efferberger, K.; Huthnacher, K.; Angew. Chem.Int.Ed.Engl. 1974, 13, 409]. The indicator attachment requires (i) preparation of the sulphonyl bromide and (ii) formation of a mixed anhydride with silver trifluoromethanesulphonate. In a second step, the reaction between the amino groups present in the porous glass and the anhydride yields the sulphonamide.

Measurement principle: Reflectance

Once the sensitive terminal is prepared, by placing it at the distal end of a fiber-optic, it was introduced into the reaction medium. In the first step, 800 ml of cyclohexane are added to the reactor (1 liter capacity) and then it is thermostated at 40° C. under stirring. Once the target temperature is reached, the reflectance spectrum of cyclohexane is collected as a reference. Subsequently, different aliquots of a cyclohexane solution of n-butyllithium (3% by weight) are added and, at the same time, the reflectance spectra of the different coloured species formed by the indicator (optical sensor) and n-butyllithium are collected in order to determine the reaction threshold.

Once the reaction threshold is determined, a cyclohexane solution of stryene is added and then n-butyllithium in stoichiometric amount required to initiate the styrene polymerization and obtaining the target molecular weight. The reaction is allowed to proceed adiabatically, with a slight increase in temperature. Confirmed the absence of styrene, the living polymer chains are terminated with a proton donor such as an alcohol.

Figure 3:
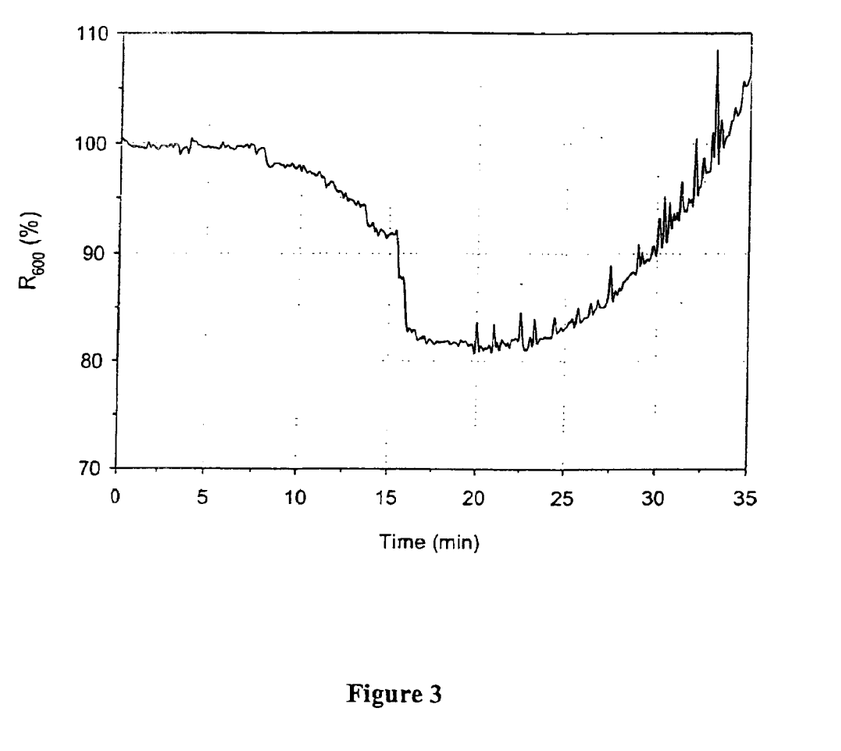
FIG. 3 shows the variation of the reflectance of the sensitive terminal based on S2D/PG during the threshold determination and during the first stage of styrene polymerization ([Styrene]$_o$=0.65 M) in clyclohexane, initiated by n-butyllithium.

In FIG. 3, we can see the variation of the reflectance of the sensitive terminal based on S2D/PG during the threshold determination and during the first stage of styrene polymerization ([Styrene]$_0$=0.65 M) in cyclohexane, initiated by n-butyllithium. The first decrease at $R_{600\ nm}$(%) (it is possible also to use other wavelengths, i.e. $R_{700\ nm}$ and $R_{450\ nm}$) is associated with the neutralization of all impurities existing in the reactor (in this case, FIG. 3, aproximately at 7 minutes of experiment record). The second step in the basal reflectance of the sensitive terminal (in this case, FIG. 3, above 15 minutes of experiment record) is associated with the addition of the monomer and n-butyllithium that will initiate the polymerization in the required amount to reach the molecular weight target.

Then, the peak molecular weight and the molecular weight distribution was determined by gel permeation chromatography based on a calibration curve of polystyrene standards, obtaining a polydispersity ratio Mw/Mn of 1.07, molecular weight peak 48000 (target 50000), showing a good fit of molecular weight after determination of the reaction threshold using this optical sensor.

Example 4

This example corresponds to a medium molecular weight styrene homopolymerization with the previous reaction threshold determination and repeteability study using an optical fiber sensor in the presence of monomer according to the object of the invention.

The active optic fiber sensor is composed by the following elements:

Indicator: 1,10-phenanthroline (PHEN)

Support: Plasticized poly(vinyl chloride) membranes (PVC).

Immobilization procedure: Embedding (physically entrapped). The membrane [Seiler, K.; "Ion-Selective Optode Membranes"; Fluka Chemie A. G., Buchs, Suiza, 1993 (Fluka Pub. No. 58166)] contains 1,10-phenanthroline as ligand and n-butyllithium titration reagent, a plasticizer [Eugster, K.; Rosatzin, T.; Rusterholz, B.; Aebersold, B.; Pedrazza, V.; Ruegg, D.; Schmid, A.; Spichiger, U.; Simon, W.; Anal.Chim.Acta. 1994, 289, 1; Okada, T.; Sugihara, H.; Hiratani, K.; Analyst, 1995, 120, 2381] (bis-(2-ethylhexyl) sebacate (DOS)) and an anionic additive (potassium tetrakis-(4-chlorophenyl)borate (KTCPB)). All the chemicals are well dissolved in tetrahydrofurane and placed in a Petri plate. Once the solvent is eliminated at room temperature, a 100 μm thick membrane is obtained.

Measurement principle: Absorbance

The sensitive terminal is prepared by placing the membrane sensor, obtained according above procedure, at the distal end of a fiber optic.

The experiments are performed in a 20 liter capacity reactor provided with an external recirculation loop with a heat-exchanger. The sensitive terminal is located in the external loop in order to make the threshold determination at the optimum measurement temperature. This is the way to keep the reactor at 60° C. (polymerization temperature) and the sensor in the external loop at 30° C.

Figure 4:
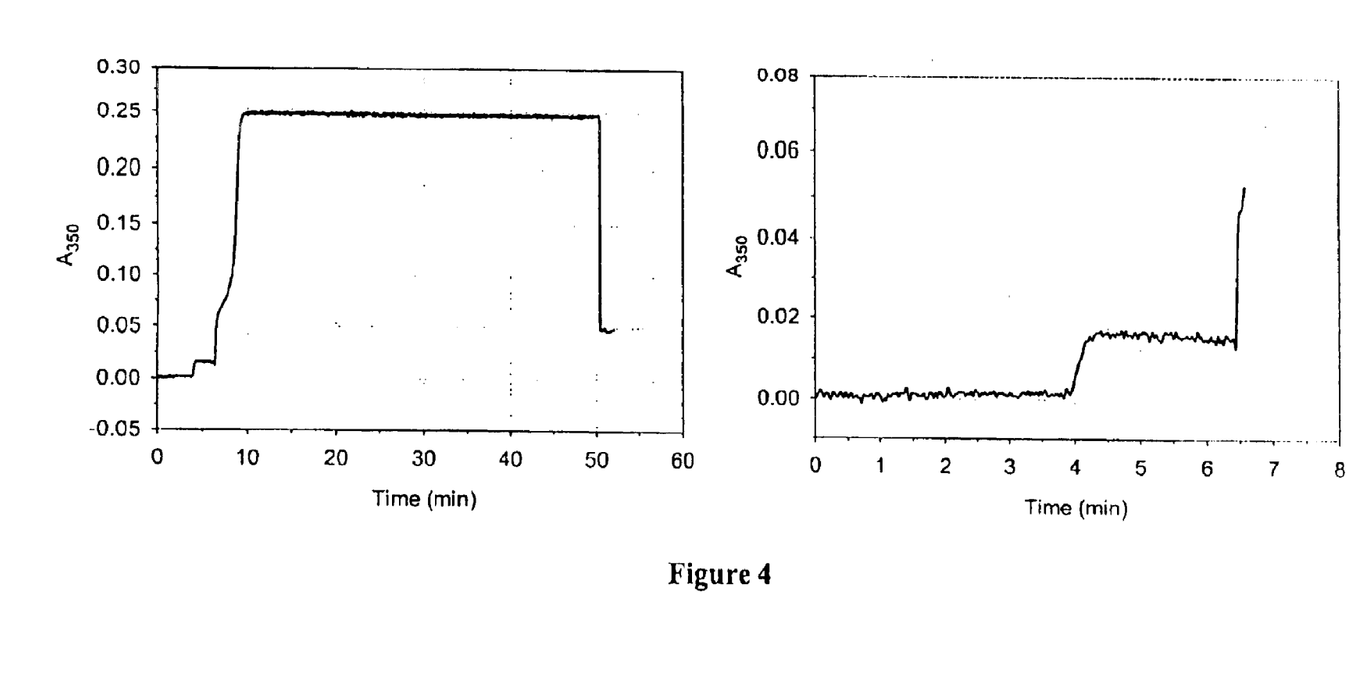
FIG. 4 shows continuously collected absorption data at 350 nm in order to determine the reaction threshold for Example 4.

In the first step, 9.5 liter of cyclohexane and 5.1 liter of a cyclohexane solution of styrene (25% by weight) are added to the reactor and then it is thermostated to 60° C. under stirring, while the external loop temperature is kept at 30° C. Once the temperature is reached, the absorption spectrum of cyclohexane and styrene is recorded as a reference. Subsequently, different aliquots of a cyclohexane solution of n-butyllithium (3% by weight) are added and, at the same time, are continuosly collected absorption data at 350 nm (similar results are obtained at other wavelengths, e.g. 400 nm, 470 nm and 520 nm) in order to determine the reaction threshold (see FIG. 4).

Once the reaction threshold is determined, what is shown by sharp slope change in absorbance data at any of the wavelengths indicated above (in this case at about 7 minutes of experiment record, see FIG. 4), a cyclohexane solution of n-butyllithium 3% (by weight) is added to initiate the polymerization of styrene in stoichiometric amount to obtain a target molecular weight of 50000 g/mol. Then, the reaction is allowed to continue adiabatically, with a slight increase in temperature. Confirmed the absence of styrene, the living polymer chains are terminated with a proton donor such as an alcohol and consequently, the absorbance values will drastically decrease because of the disappearance of the reactive species and the charge transfer complex formed in the sensitive terminal (see FIG. 4, in this cases at about 55 minutes of experiment record).

Then, the peak molecular weight and the molecular weight distribution were determined by gel permeation chromatography based on a calibration curve of polystryene standards.

These experiments were repeated ten times, with the same sensor, where different aliquots of an alcohol as a poisson of n-butyllithium were added on each reaction, such as to produce a relative standard deviation of 35% over target molecular weight. Nevertheless, through the application of threshold determination methodology described above, molecular weight obtained showed a good repeatibility. The molecular weight distributions are, in all cases, unimodal and the variability of the molecular weight of the obtained polymers (Relative Standard Deviation) is lower than 7%, in contrast with the higher value of 35% for styrene polymerization in case of no control of reaction threshold was used.

Example 5

This example corresponds to a high molecular weight styrene homopolymerization with the previous reaction threshold determination and repeatibility study using an optic fiber sensor in presence of the monomer according to the object of the invention.

The fiber-optic sensor is composed by the following elements:

Indicator: 1,10-phenanthroline (PHEN)

Support: Polyvinyl chloride membranes (PVC).

Immobilization procedure: Embedding (physically entrapped)

Measurement principle: Absorbance

The sensitive terminal is prepared by placing the membrane sensor at the distal end of a fiber-optic, obtained according to the above procedure described in example 4. The experiments are performed in a 20 liter capacity reactor provided with a external recirculation loop with a heat-exchanger. The sensitive terminal is located into the external loop in order to make the threshold determination at the optimum measurement temperature. This is the way to keep the reactor at 60° C. (polymerization temperature) and the sensor in the external loop at 30° C.

Figure 5:
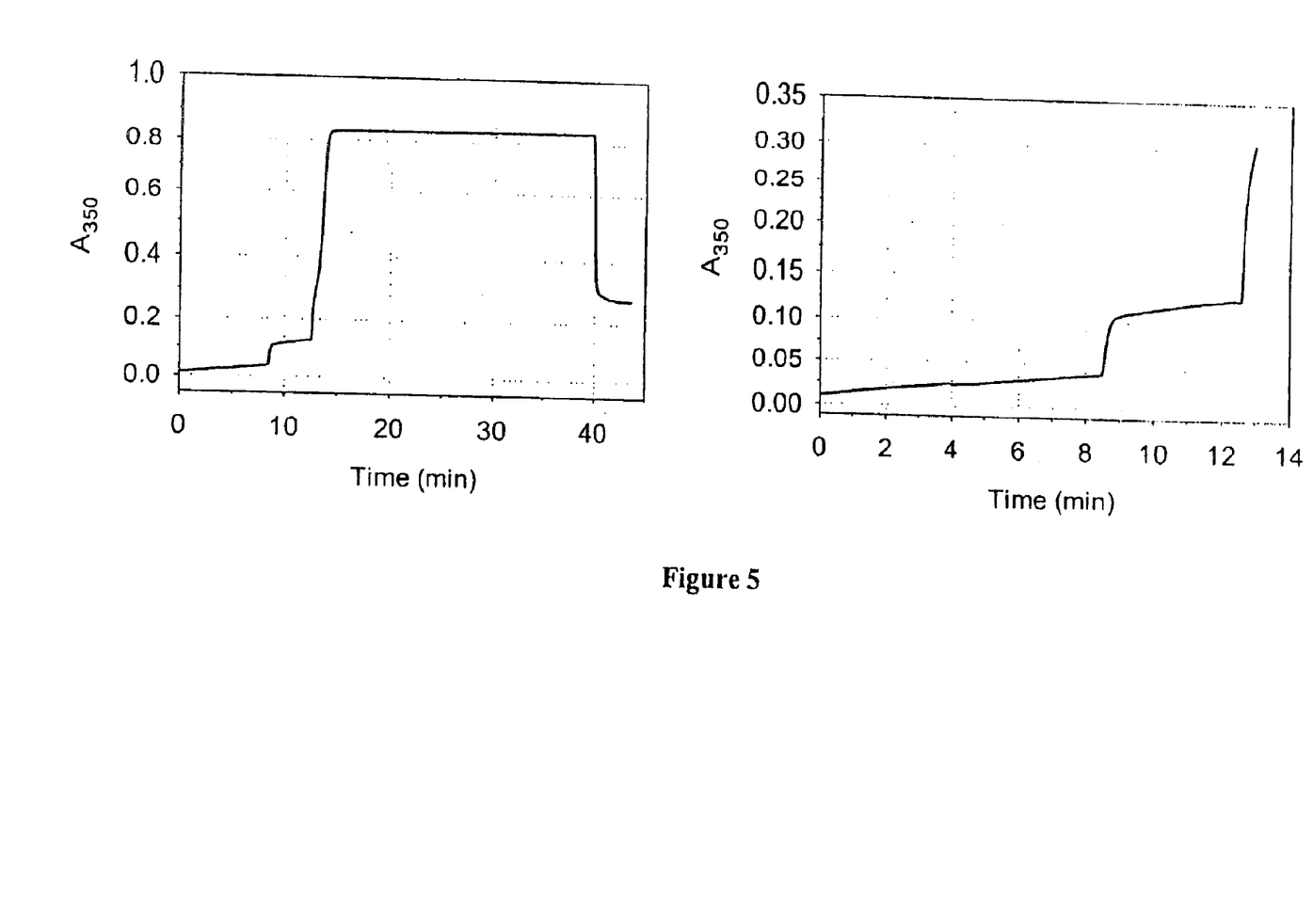
FIG. 5 shows continuously collected absorption data at 350 nm in order to determine the reaction threshold for Example 5.

In the first step, 9.6 liter of cyclohexane and 5.1 liter of a cyclohexane solution of styrene (25% by weight) are added to the reactor and then it is thermostated to 60° C. under stirring, while the external loop temperature is kept at 30° C. Once the temperature is reached, the absorption spectrum of cyclohexane and styrene is recorded as a reference. Subsequently, different aliquots of a cyclohexane solution of n-butyllithium (3% by weight) are added and, at the same time, are continuosly collected absorption data at 350 nm (similar results are obtained at other wavelengths, e.g. 400 nm, 470 nm and 520 nm) in order to determine the reaction threshold (see FIG. 5).

Once the reaction threshold is determined, what is shown by sharp slope change in absorbance data at any of the wavelengths indicated above (in this case at about 8 minutes of experiment record, see FIG. 5), a cyclohexane solution of n-butyllithium 3% (by weight) is added to initiate the polymerization of styrene in stoichiometric amount to obtain a target molecular weight of 140000 g/mol. Then, the reaction is allowed to continue adiabatically, with a slight increase in temperature. Confirmed the absence of styrene, the living polymer chains are terminated with a proton donor such as an alcohol and consequently, the absorbance values will drastically decrease because of the disappearance of the reactive species and the charge transfer complex formed in the sensitive terminal (in this case, see FIG. 5, at about 40 minutes of experiment record).

Then, the peak molecular weight and the molecular weight distribution were determined by gel permeation chromatography based on a calibration curve of polystryene standards.

These experiments were repeated ten times, with the same sensor, where different aliquots of an alcohol as a poisson of n-butyllithium were added on each reaction, such as to produce a relative standard deviation of 120% over target molecular weight. Nevertheless, through the application of threshold determination methodology described above, molecular weight obtained showed a good repeatability. The molecular weight distributions are, in all cases, unimodal and the variability of the molecular weight of the obtained polymers (Relative Standard Deviation) is lower than 7%, in contrast with the higher value of 120% for styrene polymerization in case of no control of reaction threshold was used.

What is claimed is:

1. Method for determining concentration of an organometallic compound wherein an organic medium containing the organometallic compound contacts a senior comprising
   a. an inorganic, organic or polymeric supported, insoluble in the organic medium;
   b. an indicator, which is physically trapped, adsorbed, absorbed, dissolved or chemically linked in an electrostatic or covalent way to the support, and
   c. an optical sensor; and the indicator reversibly reacts with the organometallic compound and a reaction product gives a characteristic absorption, reflectance or emission band in the range of 150–15,000 nm, and the optical sensor measures a characteristic wavelength of the absorption, reflectance or emission of the reaction product and transforms the characteristic wavelength into a concentration of the organometallic compound in the organic medium.

2. Method according to claim 1, wherein the sensor is located in a thermostated loop, maintained in constant circulation with a reactor.

3. Method according to claim 1, wherein the measurement is carried out directly in reaction medium.

4. Method according to claim 1 for determination of a neutralization point of all existing impurities that can destroy the organometallic compound.

5. Method according to claim 1 for determination of organometallic compounds in industrial and laboratory chemical synthesis.

6. Method according to claim 1, wherein the concentration of the organometallic compound in reaction medium is determined on-line.

7. Method according to claim 1 for determination of a neutralization point of all existing impurities that can destroy an organometallic initiator in an anionic polymerization.

8. Method according to claim 1 for determination of neutralization points of all existing impurities that can destroy an organometallic initiator in an anionic polymerization of a 1,3-conjugated diene and/or monoalkenyl aromatic hydrocarbon copolymer.

9. Method according to claim 1 for determination of neutralization points of all existing impurities that can destroy an organometallic initiator in an anionic polymerization of a 1,3-conjugated diene and/or monoalkenyl aromatic hydrocarbon copolymer initiated by organolythium compounds.

10. Method according to claim 1 for determination of a neutralization point of all existing impurities that can destroy an organometallic initiator in the anionic polymerization wherein the organometallic compound is titrated and the neutralization point is monitored.

* * * * *